(12) United States Patent
Wang et al.

(10) Patent No.: US 10,039,713 B1
(45) Date of Patent: Aug. 7, 2018

(54) DRUG-LOADED GANGLIOSIDE MICELLE AND THE PREPARATION METHOD AND USE THEREOF

(71) Applicant: Chongqing University, Chongqing (CN)

(72) Inventors: Yazhou Wang, Chongqing (CN); Dan Zou, Chongqing (CN); Tieying Yin, Chongqing (CN); Guixue Wang, Chongqing (CN)

(73) Assignee: Chongqing University, Chongqing, Sichuan Province (CN)

( * ) Notice: Subject to any disclaimer, the term of this patent is extended or adjusted under 35 U.S.C. 154(b) by 0 days.

(21) Appl. No.: 15/871,300

(22) Filed: Jan. 15, 2018

(30) Foreign Application Priority Data

Mar. 14, 2017 (CN) .......................... 2017 1 0150621

(51) Int. Cl.

| | | |
|---|---|---|
| *A61K 9/00* | (2006.01) | |
| *A61K 38/38* | (2006.01) | |
| *A61K 38/00* | (2006.01) | |
| *A61K 31/70* | (2006.01) | |
| *A61K 9/107* | (2006.01) | |
| *A61K 47/26* | (2006.01) | |
| *A61K 31/65* | (2006.01) | |
| *A61K 31/12* | (2006.01) | |
| *A61P 35/00* | (2006.01) | |
| *A61P 25/08* | (2006.01) | |
| *A61P 25/28* | (2006.01) | |
| *A61P 9/12* | (2006.01) | |
| *A61P 25/24* | (2006.01) | |
| *A61P 25/00* | (2006.01) | |

(52) U.S. Cl.
CPC ............ *A61K 9/1075* (2013.01); *A61K 31/12* (2013.01); *A61K 31/65* (2013.01); *A61K 47/26* (2013.01); *A61P 9/12* (2018.01); *A61P 25/00* (2018.01); *A61P 25/08* (2018.01); *A61P 25/24* (2018.01); *A61P 25/28* (2018.01); *A61P 35/00* (2018.01)

(58) Field of Classification Search
CPC ........ A61K 47/10; A61K 38/38; A61K 38/00; A61K 31/70; A61K 31/337

USPC .................... 424/400; 514/15.2, 17.8, 25, 37
See application file for complete search history.

(56) References Cited

U.S. PATENT DOCUMENTS

| | | | | |
|---|---|---|---|---|
| 9,895,440 | B2 * | 2/2018 | Weiner ............... | A61K 39/3955 |
| 2011/0044902 | A1 * | 2/2011 | Weiner ................ | A61K 31/405 |
| | | | | 424/9.1 |
| 2014/0171372 | A1 * | 6/2014 | Lalezari ............. | A61K 31/7032 |
| | | | | 514/17.8 |
| 2016/0053271 | A1 * | 2/2016 | Gramajo ............... | C12P 7/6436 |
| | | | | 435/252.3 |

OTHER PUBLICATIONS

Dan Zou et al., Penetration of blood—brain barrier and antitumor activity and nerve repair in glioma by doxorubicin-loaded monosialoganglioside micelles system, International Journal of Nanomedicine, Jul. 7, 2017, P4879-P4889, Dove Medical Press Limited.

* cited by examiner

*Primary Examiner* — Raymond J Henley, III
(74) *Attorney, Agent, or Firm* — IPro, PLLC; Na Xu; Qian Gu

(57) ABSTRACT

The present application belongs to the field of biopharmaceutical technology and particularly relates to a drug-loaded ganglioside micelle and a method for preparing and use thereof. The present application provides a use of GM1 or a derivative thereof as a carrier material of nano drug delivery system. The blood brain barrier is a key barrier to intracranial drug delivery. The nano drug delivery system provides a powerful tool for non-invasive intracranial combined administration and has important clinical significance. Without introducing other carrier materials, long-circulating modifying materials and nerve repair drugs, the drug-loaded ganglioside micelle prepared by using GM1 or a derivative thereof as a carrier material of nano drug delivery system can achieve nerve injury repair and intracranial combined administration by penetrating the blood-brain barrier. The drug-loading ganglioside micelle in the present application is expected to provide a new perspective and method for improving clinical treatment.

17 Claims, 1 Drawing Sheet

DRUG-LOADED GANGLIOSIDE MICELLE AND THE PREPARATION METHOD AND USE THEREOF

TECHNICAL FIELD

The present application belongs to the technical field of biopharmaceutical materials, and particularly relates to a drug-loaded ganglioside micelle and the preparation method and use thereof.

BACKGROUND

In pharmacotherapy, almost all of the macromolecular drugs and many small molecules drugs cannot enter the brain and central nervous system due to the existence of the blood brain barrier (BBB). Whether the drug can be delivered to penetrating the blood brain barrier and still reaching an effective therapeutic concentration is critical for the treatment of glioma. After traditional administration of chemical treatment drugs, the drugs cannot directly and effectively act on lesions due to the physiological response of the subject itself. The blood brain barrier is a key barrier for intracranial drug delivery for treating brain diseases.

The so-called blood brain barrier is a selective permeable "Neurovascular Unit" (NVU) composed of a specific physical structure, various enzymes and transporters. Its anatomical structures of specific barrier is selected from the group consisting of: endothelial cell layer closely jointed by brain capillary, continuous basement membrane layer outside of the endothelial cells, pericytes in the outer wall of the cerebral capillaries, and astrocyte end-feet, which constitute a barrier between the blood and brain tissue that has important significance to maintain the homeostasis of brain tissue and the normal physiological function of intracranial central nervous system (CNS). In brain diseases, brain gliomas (gliomas) account for about 46 percent of intracranial tumors and 1 to 3 percent of all malignant tumors of the whole body. With extremely high mortality and recurrence rates, gliomas seriously threaten human health. In clinical treatment of malignant glioma, the priority is still given to surgery supplemented with radiotherapy and chemotherapy. Because of the presence of the blood brain barrier, 98% of small molecular and almost all of macromolecular drugs cannot reach to the intracranial tumor tissue. Therefore, how to penetrate the Blood Brain Barrier (BBB) is the key to realize the new strategy of nerve injury repair and antitumor combined administration.

GM1 (Ganglioside M1) is one of the most important gangliosides, which is the main type of mammalian gangliosides and has the highest content in CNS gray matter. Endogenous GM1 is the main component of nerve cell membrane and plays an important role in nerve cell differentiation, regeneration and signal transmission, and most of the neurodegeneration and injuries are associated with the absence of GM1. Studies have shown that the supplementation of exogenous GM1 has beneficial effects on promoting nerve reparation and regeneration to nerve injury caused by ischemia, hypoxia, drug toxicity and trauma. Its effectiveness, high safety and high tolerance dose have been widely proven in the clinical treatment of cerebral apoplexy, brain trauma, Parkinson and other neurodegenerative diseases. GM1 is the only exogenous ganglioside that can penetrate the blood brain barrier and has been proved to play an important physiological role in the differentiation, growth and regeneration of nerve cells. However, currently no relevant literature has shown that drug-loaded GM1 micelle is used for administration of intracranial drug by penetrating blood-brain barrier.

Therefore, with its characteristics of BBB penetrating, nerve injury repairing and high security, GM1 will be a carrier material of a nano drug delivery system for treating malignant tumors and penetrating other intracranial blood-brain barriers.

SUMMARY

In view of this, an objective of the present application is to provide a new use of GM1 or a derivative thereof as a carrier material of nano drug delivery system. Without introducing other carrier materials, long-circulating modified materials and nerve repair drugs, the drug-loaded ganglioside micelle prepared by using the GM1 or a derivative thereof as a carrier material of nano drug delivery system can be used to penetrate the blood-brain barrier to achieve nerve injury reparation and intracranial administration.

To achieve the above objective, the technical solution of the present application is: use of GM1 or a derivative thereof as a carrier material of nano drug delivery system.

Further, the derivatives of GM1 is selected from the group consisting of LIGA20, LIGA4 (N-acetyl sphingosine) and PKS3 (d-eritro 1, 3-dihydroxy-2-dichloroacetylamide-4-trans-octadecene).

LIGA is made by replacing a long-chain fatty acid on ceramide of GM1 with dichloroacetyl.

GM1 analogues are used as a carrier material of nano drug delivery system. The GM1 analogue is selected from the group consisting of GM1, GM2, GM3 and GD1. The mentioned GM1 analogues all belong to ganglioside, they all have an effect on brain nerves, and they are all amphipathic molecules. After being modified, the analogues can penetrate the BBB and also can be used as a carrier material of nano drug delivery system.

Nano carrier materials within the brain tissue cannot be degraded, and their accumulation or inaccurate degradation metabolic pathways are bound to cause the risk of microenvironment change; however, homeostasis in the brain is closely related to the normal physiological function of brain homeostasis and central nervous system, which makes the selection of carrier materials for intracranial nano drug delivery system very important. The structure of GM1 shows that GM1 is an amphipathic molecule which can be easily prepared into micelle of different particle sizes under 100 nm through self-assembly. With its good BBB penetrating characteristic and high security, GM1 will become a carrier material of nano drug delivery system for treating malignant tumors and penetrating other intracranial blood-brain barriers.

The second objective of the present application is to provide a drug-loaded ganglioside micella prepared by using GM1 or a derivative thereof as a nano drug delivery system carrier.

The nano drug delivery system is used for loading a drug, selected from the group consisting of a drug for treating an intracranial disease and a drug for treating a central nervous system disease.

Further, the drug for treating an intracranial disease or a central nervous system disease is selected from the group consisting of: an intracranial antitumor drug, an antidepressant, an antiepileptic drug, a drug against neurodegenerative disease, a drug against intracranial hematoma and a drug against blood pressure.

In the present application, the drug against a brain disease belongs to an intracranial drug, including a drug and a nutrition factor treating a degenerative disease; the intracranial drug is selected from the group consisting of: DOX, CUR, Ptx, Dtx, β-carotene and lamotrigine.

Unlike tumors in other tissues, the specific tissue structures and functions of BBB are key barriers to drug delivery. Based on the characteristics of BBB penetrating, amphipathy, nerve repairing, high security and high tolerance, GM1 or a derivative thereof, and in combination with the scale effect and mediated transportation of a nanometer carrier, nano micelle of self-assembled GM1 or a derivative thereof are prepared to carry intracranial antitumor drug in order to achieve non-invasive nerve injury reparation and antitumor combined administration. The present application is expected to provide a new theoretical and experimental basis for improving the treatment against a malignant glioma, even for the clinical treatment against a central nervous system.

Adriamycin (Doxorubicin, DOX) is a kind of antitumor antibiotics, and can inhibit the synthesis of RNA and DNA. It has a stronger inhibitory effect on RNA. It has a broad antineoplastic spectrum, which means that it has effects on a wide variety of tumors; it belongs to a non-specific cycle drug, which means that it can kill tumor cells in different periods of growth cycle. It is mainly used for treating acute leukemia, and is effective for acute lymphocytic leukemia and acute myeloid leukemia. It is commonly used as a second-line medicine, which will be administrated after the subject is resisted to the first-choice drug. For malignant lymphoma, DOX can be administrated as a first-choice drug for alternate use. It also has curative effects on a breast cancer, a sarcoma, a lung cancer, a bladder cancer and other cancers.

Curcumin (curcumin, CUR): is a kind of yellow pigment extracted from a rhizome of turmeric or other plants, which belongs to zingiberaceae. It is insoluble in water and ether but is soluble in ethanol and glacial acetic acid. It has effects selected from the group consisting of anti-inflammatory, antioxidation, antitumor and other pharmacological effects. It has the function of preventing cardiovascular disease, and delaying senescence.

Lamotrigine (LTG) is an antiepileptic drug.

Further, the drug-loading ganglioside micelle comprises a DOX-GM1 micelle, a CUR-GM1 micelle and/or a DOX-LIGA micelle.

The third objective of the present application is to provide a method for preparing a drug-loaded ganglioside micelle, comprising:

1) adequately dissolving GM1 and/or a derivative thereof in a solvent medium, centrifuging and filtering, then allowing it to stand still, and obtaining a solution of GM1 and/or a derivative thereof.

2) adequately dissolving an intracranial drug in an organic solvent, and obtaining an intracranial drug solution;

3) adding the intracranial drug solution obtained in 2) to the solution of GM1 and/or a derivative thereof obtained in 1), stirring and mixing well, then incubating at 2° C.~8° C., and obtaining a mixed solution;

4) transferring the mixed solution obtained in 3) to a dialysis bag for dialysis, and keeping the dialyzed solution still at 2° C.~8° C. to obtain a drug-loaded ganglioside micelle.

The solvent medium in 1) comprises water and an organic solvent; the organic solvent in 2) comprises: dimethyl sulfoxide solution, dimethylformamide and tetrahydrofuran.

The objective of the present application is also to provide a method for preparing a DOX-GM1 micelle, comprising:

1) adequately dissolving GM1 in a solvent medium, centrifuging and filtering, then allowing it to stand still to obtain a GM1 solution;

2) adequately dissolving DOX in an organic solvent, and obtaining a DOX solution;

3) adding the DOX solution obtained in 2) to the GM1 solution obtained in 1), stirring and mixing well, then incubating at 2° C.~8° C., and obtaining a mixed solution;

4) transferring the mixed solution obtained in 3) to a dialysis bag for dialysis, and keeping the dialyzed solution still at 2° C.~8° C. to obtain a DOX-GM1 micelle.

The solvent medium in 1) comprises water and an organic solvent; the organic solvent in 2) comprises: dimethyl sulfoxide solution, dimethylformamide and tetrahydrofuran.

Without introducing other carrier materials, long-circulating modified materials and nerve repair drugs, the drug-loaded ganglioside micelle prepared by using the GM1 as a carrier material of nano drug delivery system can be used to penetrate the blood-brain barrier with high security to achieve nerve injury reparation and intracranial antitumor combined administration.

A DOX-GM1 micelle is with the particle size of less than 100 nm.

Preferably, the particle size of the DOX-GM1 micelle is 10~100 nm. Further, a molar ratio of the GM1 in 1) to the DOX in 2) is 2~20:1; in 1), after adequately dissolving the GM1 in the solvent medium, keeping it at 2° C.~8° C. for 22~26 hours, then centrifuging for 25~35 minutes, then filtering the solution and keeping it at 2° C.~8° C. for 22~26 hours, to obtain the GM1 solution; in 3), the time for incubating is 22~26 hours; in 4), the time for dialysis is 22~26 hours.

A mole ratio of the GM1 to the DOX is within the range of 2~20:1 in order to obtain a better drug loading capacity and entrapment rate. Allowing to stand still at low temperature and maintaining for a period are designed in the present application to form a uniform and stable micelle.

The DOX-GM1 micelle can be used in the preparation of an intracranial antitumor drug. After allowing it to stand still at 4° C. for 24 hours, the DOX-GM1 micelle made by the method of preparation can be used as intravenous injection preparation for an experiment.

The present application is further intended to provide use of the drug-loaded ganglioside micelle to preparation of an intracranial drug. The intracranial drug is used for a brain disease, selected from the group consisting of an intracranial antitumor drug, an intracranial anti-depressant drug, an intracranial anti-hematoma drug and an anti-blood pressure drug. In the present application, the drugs for treating a brain disease all belong to the intracranial drug, selected from the group consisting of drugs and nutrition factors for treating degenerative diseases; the intracranial drug comprises DOX, CUR, Ptx, Dtx, β-carotene and lamotrigine (Lamotrigine, LTG).

The beneficial effects of the application are:

1) The present application provides a new use of a GM1 or a derivative thereof as a carrier material of nano drug delivery system. The blood-brain barrier is a key barrier to intracranial drug delivery. The nano drug delivery system provides a powerful tool for non-invasive intracranial combined administration and has important clinical significance.

2) The DOX-GM1 micelle of the present application has a particle size being less than 100 nm. The micelle combines nerve injury reparation and anti-tumor effects in the treatment of malignant glioma or other intracranial tumors. It is expected to provide a new perspective and method to improve the clinical treatment.

3) The DOX-GM1 micelle can be prepared simply and can be used to penetrate the blood-brain barrier with high security to achieve nerve injury repair and intracranial antitumor combined medication, without introducing other carrier materials, long-circulating modified materials and nerve repair drugs.

DETAILED DESCRIPTION

Figure 1:
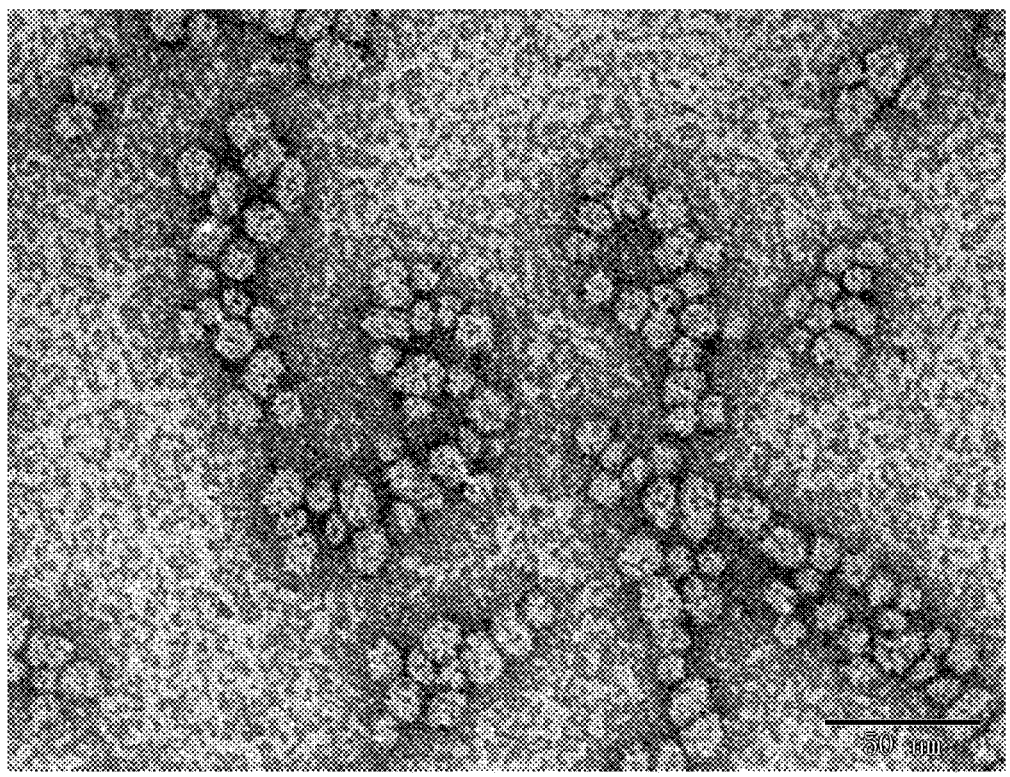
FIG. 1 shows a transmission electron micrograph of a DOX-GM1 micelle, indicating that the micelle has a relatively homogeneous spheroid.

The following is detailed description of the preferred embodiments of the present application in connection with accompany drawings. Experimental methods without specific conditions in the preferred embodiments are typically carried out under conventional conditions. The embodiments are described to better illustrate the contents of the present application, but it does not mean that the content of the present application is limited to the embodiments described. It will be understood by those skilled in the art that non-essential improvements and adjustments made to solutions of the embodiments according to the above-mentioned content of the present application are still within the scope of the present application.

Example 1 Preparation of a DOX-GM1 Micelle

Preparation of micelle: a DOX-GM1 micelle was prepared by dialysis. GM1 powder was weighed precisely and was put in beaker. The adequate tri-distilled water was added into the beaker. It was stirred until fully dissolved; then the GM1 solution was placed at 4° C. in a refrigerator for about 20 hours, and was centrifuged for 30 minutes, then the solution was filtered and placed at 4° C. in refrigerator for about 20 hours for possible further use; Weighed DOX powder was fully dissolved in organic solvents. Dox solution was slowly added to GM1 while stirring; Mixed DOX-GM1 solution was incubated at 4° C. in refrigerator for about 20 hours. And then the solution was transferred to the dialysis bag to dialyze for 24 hours, finally the DOX-GM1 solution was stood at 4° C. in a refrigerator for 24 hours for the further use in the experiment.

Example 2 Preparation of a DOX-LIGA Micelle

LIGA powder was weighed precisely and was put in beaker. The adequate tri-distilled water was added into the beaker. It was stirred until fully dissolved; Then the LIGA solution was placed at 4° C. in a refrigerator for about 20 hours, and was centrifuged for 30 minutes, then the solution was filtered and placed at 4° C. in a refrigerator for about 20 hours for possible further use; weighed DOX powder was fully dissolved in organic solvents. Dox solution was slowly added to LIGA while stirring; mixed DOX/LIGA solution was incubated at 4° C. in refrigerator for about 20 hours after mixing. And then the solution was transferred to the dialysis bag to dialyze for 24 hours, finally the DOX-LIGA solution was stood at 4° C. in refrigerator for 24 hours for the further use in the experiment.

Example 3 Preparation of a CUR-GM1 Micelle

GM1 powder was weighed precisely and was put in beaker. The adequate tri-distilled water was added into the beaker. It was stirred until fully dissolved; Then the GM1 solution was placed at 4° C. in a refrigerator for about 20 hours, and was centrifuged for 30 minutes, then the solution was filtered and placed at 4° C. in refrigerator for about 20 hours for possible further use; Weighed curcumin powder was fully dissolved in organic solvents. Curcumin solution was slowly added to GM1 with stirring; Mixed CUR-GM1 solution was incubated at 4° C. in refrigerator for about 20 hours. And then the solution was transferred to the dialysis bag to dialyze for 24 hours, finally the CUR-GM1 solution was stood at 4° C. in refrigerator for 24 hours for the further use in the experiment.

Example 4 Evaluation on Intracranial Blood Brain Barrier Penetrating Effect of a GM1 Micelle According to the preparation method of DOX-GM1 in the example 1, a fluorescent dye DiR-GM1 mixed micelle was prepared according to the same method. DiR-GM1 micelle and free-DiR were intravenous injected of tails of the healthy mice. The distribution and strength of the DiR fluorescence in tissues are observed and recorded by the animal living body imagery at different time points.

Figure 2:
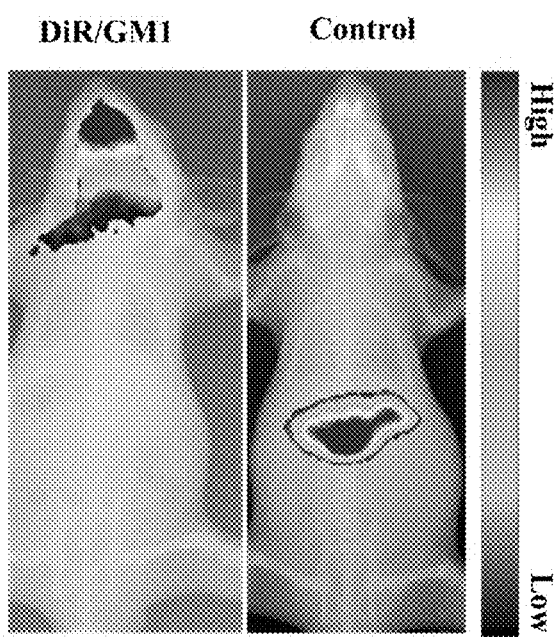
FIG. 2 shows in-vivo fluorescence profiles of mice after the injection of a DiR/GM1 micelle solution and a DiR fluorescent solution (control group).

As shown in FIG. 2, the fluorescence distribution of the control group (DiR solution) was concentrated in the liver of mice, illustrating that the DiR solution cannot enter the brain after being injected into the body of mice by intravenous injection of tails, instead, it was engulfed by the phagocytes of liver reticuloendothelial tissue, so it was confirmed that the blood brain barrier prevents the vast majority of drugs into the brain. However, the fluorescence distribution in the experimental group (DiR/GM1) was mainly concentrated in the brain, indicating that GM1 micelles can transfer the fluorescent substance DiR into the brain which penetrated the blood-brain barrier.

Finally, to be noted that the foregoing embodiments are merely illustrative of the technical solutions of the present application and are not intended to be interpret as limiting the present application. Although the present application has been described in detail with reference to preferred embodiments, it should be understood by those of the skilled in the art that the technical solution of the present application may be modified or equivalently replaced, without departing from the spirit and scope of the technical solution of the present application, which is intended to be included within the scope of the claims of the present application.

What is claimed is:
1. A method comprising:
  obtaining a first solution of Ganglioside M1 (GM1), II$^3$—N-acetylneuraminosylgangliotetraosyl-D-erythro-1,3-dihydroxy-2-2dichloroacetylamide-4-trans-octadacene (LIGA20), N-acetyl sphingosine (LIGA4) or d-eritro 1, 3-dihydroxy-2-dichloroacetylamide-4-trans-octadecene (PKS3);
  obtaining a second solution of a drug;
  obtaining a mixed solution by mixing the first solution and the second solution; and
  obtaining drug-loaded ganglioside micelles by dialyzing the mixed solution.

2. The method according to claim 1, wherein the drug is selected from the group consisting of a drug for treating an intracranial disease and a drug for treating a central nervous system disease.

3. The method according to claim 2, wherein the drug for treating an intracranial disease or the drug for treating a central nervous system disease is selected from the group consisting of an intracranial antitumor drug, an antidepressant, an antiepileptic drug, a drug against a neurodegenerative disease, a drug against an intracranial hematoma and a drug against blood pressure.

4. The method according to claim 1, wherein the drug comprises doxorubicin (DOX) or curcumin (CUR).

5. The method according to claim 1, wherein obtaining the mixed solution comprises incubation at a temperature between 2° C. and 8° C.

6. The method according to claim 1, wherein dialyzing the mixed solution is at a temperature between 2° C. and 8° C.

7. The method according to claim 1, wherein a molar ratio of GM1 to the drug is between 2:1 and 20:1.

8. The method of claim 1, further comprising incubating the first solution at a temperature between 2° C. and 8° C. for a time period between 22 hours and 26 hours.

9. The method of claim 1, further comprising centrifuging the first solution for a time period between 25 minutes and 35 minutes.

10. The method of claim 1, further comprising filtering the first solution.

11. The method according to claim 1, wherein dialyzing the mixed solution is for a duration between 22 hours and 26 hours.

12. The method according to claim 5, wherein the incubation is for a duration between 22 hours and 26 hours.

13. A micelle comprising:
an enclosure comprising Trisialoganglioside-GT1b (GM1), LIGA20, N-acetyl sphingosine or d-eritro 1,3-dihydroxy-2-dichloroacetylamide-4-trans-octadecene; and
a drug in the enclosure.

14. The micelle of claim 13, wherein the drug comprises doxorubicin (DOX) or curcumin (CUR).

15. The micelle of claim 13, wherein a molar ratio of GM1 to the drug is between 2:1 and 20:1.

16. The micelle of claim 13, wherein the drug is selected from the group consisting of a drug for treating an intracranial disease and a drug for treating a central nervous system disease.

17. The micelle of claim 16, wherein the drug for treating an intracranial disease or the drug for treating a central nervous system disease is selected from the group consisting of: an intracranial antitumor drug, an antidepressant, an antiepileptic drug, a drug against a neurodegenerative disease, a drug against an intracranial hematoma and a drug against blood pressure.

* * * * *